United States Patent
Markovitz et al.

(10) Patent No.: US 8,865,867 B2
(45) Date of Patent: Oct. 21, 2014

(54) LECTINS AND USES THEREOF

(75) Inventors: David Markovitz, Ann Arbor, MI (US); Michael Swanson, Ann Arbor, MI (US); Irwin Goldstein, East Ann Arbor, MI (US); Harry Winter, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 13/640,498

(22) PCT Filed: Apr. 11, 2011

(86) PCT No.: PCT/US2011/031895
§ 371 (c)(1),
(2), (4) Date: Nov. 27, 2012

(87) PCT Pub. No.: WO2011/130145
PCT Pub. Date: Oct. 20, 2011

(65) Prior Publication Data
US 2013/0096051 A1    Apr. 18, 2013

Related U.S. Application Data

(60) Provisional application No. 61/324,107, filed on Apr. 14, 2010.

(51) Int. Cl.
| | | |
|---|---|---|
| *C07K 14/00* | (2006.01) | |
| *A61K 38/16* | (2006.01) | |
| *A61P 31/12* | (2006.01) | |
| *A61P 31/18* | (2006.01) | |
| *A61K 38/00* | (2006.01) | |
| *C07K 14/42* | (2006.01) | |

(52) U.S. Cl.
CPC *C07K 14/42* (2013.01); *A61K 38/00* (2013.01)
USPC ............ 530/350; 514/21.2; 514/3.7; 514/3.8; 514/1.1

(58) Field of Classification Search
None
See application file for complete search history.

(56) References Cited

PUBLICATIONS

Swanson et al: "A Lectin Isolated from Bananas Is a Potent Inhibitor of HIV Replication", Journal of Biological Chemistry, vol. 285, No. 12, Mar. 19 2818 (2818-83-19), pp. 8646-8655.*
Cheung et al. "*Musa acuminata* (Del Monte banana) lectin is a fructose-binding lectin with cytokine-inducing activity", Phytomedicine, Gustav Fischer Verlag, Stuttgart, DE, vol. 16, No. 6-7, Jun. 1, 2009, pp. 594-600.*
Clendennen et al. "Differential Gene Expression in Ripening Banana Fruit" Plant Physiology, American Society of Plant Physiologists, Rockville, MD, US, vol. 115, No. 2, Oct. 1, 1997, pp. 463-469.*
Meagher et al. "Crystal structure of banana lectin reveals a novel second sugar RT binding site." Glycobiology 15:1033-1042(2005).*
Swanson et al., "A lectin isolated from bananas is a potent inhibitor of HIV replication." J Biol Chem. Mar. 19, 2010; 285(12):8646-55.
Darville et al., "Complete nucleotide sequence coding for rat liver 6-phosphofructo-2-kinase/fructose-2,6-bisphosphatase derived from a cDNA clone." FEBS Lett. Nov. 30, 1987; 224(2):317-21.
Meagher et al., "Crystal structure of banana lectin reveals a novel second sugar binding site." Glycobiology. Oct. 2005; 15(10):1033-42.
Singh et al., "Unusual sugar specificity of banana lectin from *Musa paradisiaca* and its probable evolutionary origin. Crystallographic and modelling studies." Glycobiology. Oct. 2005; 15(10):1025-32.
Jeyaprakash et al., "Structural basis for the carbohydrate specificities of artocarpin: variation in the length of a loop as a strategy for generating ligand specificity." J Mol Biol. May 7, 2004; 338(4):757-70.
Nakumura-Tsuruta et al., "Analysis of the sugar-binding specificity of mannose-binding-type Jacalin-related lectins by frontal affinity chromatography—an approach to functional classification." FEBS J. Mar. 2008; 275(6):1227-39.
Santoni De Sio & Trono, "APOBEC3G-depleted resting CD4+ T cells remain refractory to HIV1 infection." PLoS One. Aug. 10, 2009;4(8):e6571.
Cheung et al., "*Musa acuinata* (Del Monte banana) lectin is a fructose-binding lectin with cytokine-inducing activity." Phytomedicine, Gustav Fisher Verlag, Stuttgart, DE, Jun. 1, 2009, 16(No. 6-7).
Database UniProt, Jan. 1, 1998, Database accession No. 022321 abstract, Clendennen et al., "Differential Gene Expression in Ripening Banana Fruit." Plant Physiology, American Society of Plant Physiologists Oct. 1, 1997, 1 page.

* cited by examiner

*Primary Examiner* — Maury Audet
(74) *Attorney, Agent, or Firm* — Casimir Jones SC

(57) ABSTRACT

The present invention relates to chemical compounds, methods for their discovery, and their therapeutic and research use. In particular, the present invention provides antiviral and antimicrobial lectin compounds (BanLec) isolated from bananas. These compounds have low mitogenicity and pro-inflammatory activity while maintaining anti-HIV-1 activity.

7 Claims, 13 Drawing Sheets

B

D

FIGURE 9

Figure 1:
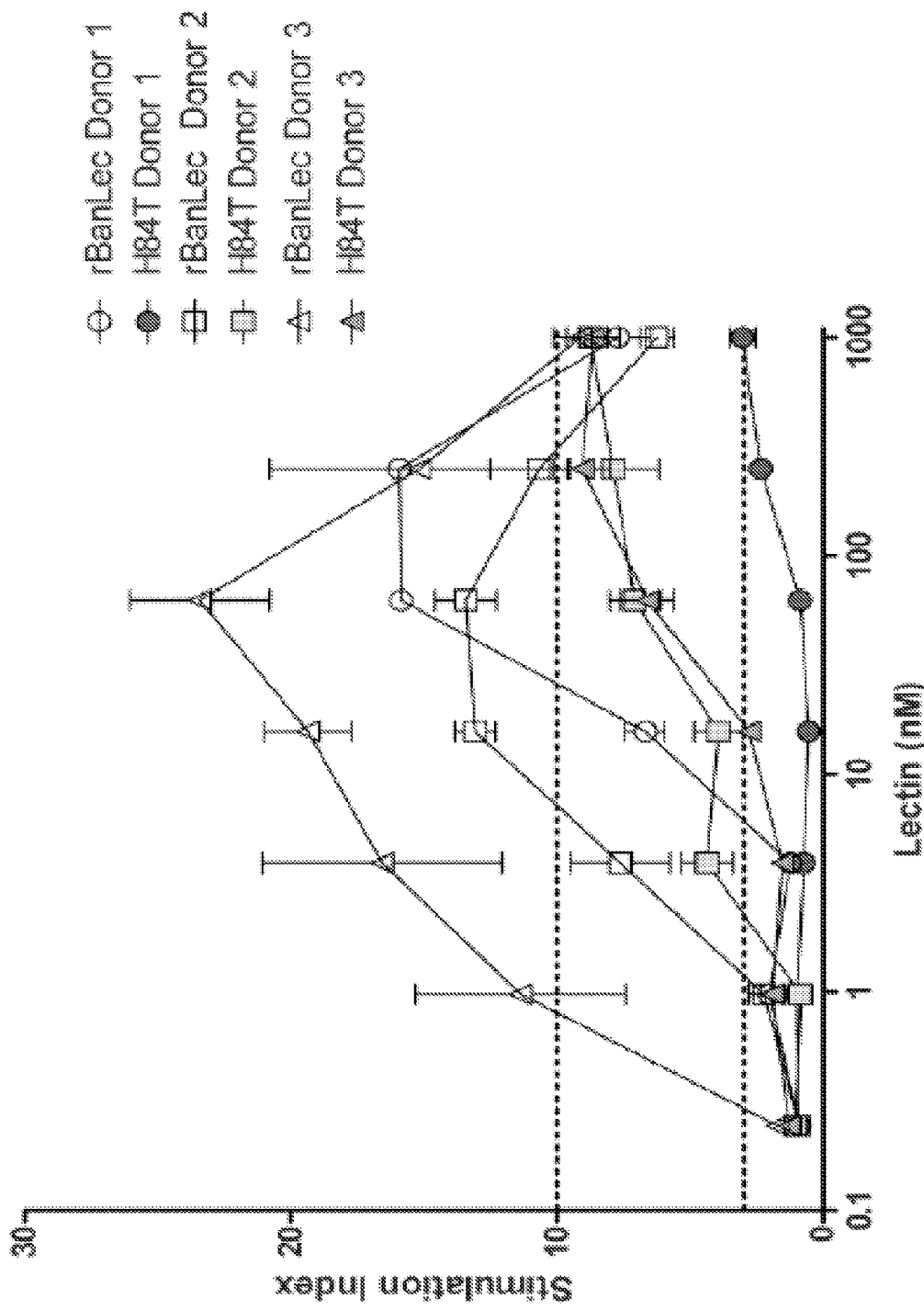

>H84T (SEQ ID NO:1)
MNGAIKVGAWGGNGGSAFDMGPAYRIISVKIFSGDVVDGVDVTFTYYGKTETR
HYGGSGGTPHEIVLQEGEYLVGMAGEVANYTGAVVLGKLGFSTNKKAYGPFGN
TGGTPFSLPIAAGKISGFFGRGGKFLDAIGVYLEPLE

>H84S (SEQ ID NO:2)
MNGAIKVGAWGGNGGSAFDMGPAYRIISVKIFSGDVVDGVDVTFTYYGKTETR
HYGGSGGTPHEIVLQEGEYLVGMAGEVANYSGAVVLGKLGFSTNKKAYGPFGN
TGGTPFSLPIAAGKISGFFGRGGKFLDAIGVYLEPLE

>H84M (SEQ ID NO:3)
MNGAIKVGAWGGNGGSAFDMGPAYRIISVKIFSGDVVDGVDVTFTYYGKTETR
HYGGSGGTPHEIVLQEGEYLVGMAGEVANYMGAVVLGKLGFSTNKKAYGPFG
NTGGTPFSLPIAAGKISGFFGRGGKFLDAIGVYLEPLE

The DNA sequences of BanLec mutants. Mutations are highlighted.
>H84T (SEQ ID NO:4)
ATGAATGGTGCGATCAAAGTTGGCGCGTGGGGTGGCAACGGTGGTAGCGCCT
TTGATATGGGCCCGGCGTATCGTATTATTAGCGTGAAAATTTTTAGCGGTGAT
GTGGTTGATGGCGTTGATGTGACCTTTACCTATTATGGTAAAACCGAAACCCG
TCATTATGGCGGTAGCGGTGGTACCCCGCATGAAATTGTGCTGCAGGAAGGT
GAATATCTGGTGGGTATGGCGGGCGAAGTGGCGAACTATACTGGTGCGGTGG
TGCTGGGTAAACTGGGTTTTAGCACCAATAAAAAAGCGTATGGTCCGTTTGG
CAATACCGGCGGTACCCCGTTTAGCCTGCCGATTGCCGCGGGTAAAATTAGC
GGCTTCTTTGGTCGTGGCGGTAAATTCTGGATGCCATTGGCGTGTATCTGGA
ACCGCTCGAGTGA >H84S (SEQ ID NO:5)
ATGAATGGTGCGATCAAAGTTGGCGCGTGGGGTGGCAACGGTGGTAGCGCCT
TTGATATGGGCCCGGCGTATCGTATTATTAGCGTGAAAATTTTTAGCGGTGAT

FIGURE 9 (cont.)

GTGGTTGATGGCGTTGATGTGACCTTTACCTATTATGGTAAAACCGAAACCCG
TCATTATGGCGGTAGCGGTGGTACCCCGCATGAAATTGTGCTGCAGGAAGGT
GAATATCTGGTGGGTATGGCGGGCGAAGTGGCGAACTATAGTGGTGCGGTGG
TGCTGGGTAAACTGGGTTTTAGCACCAATAAAAAAGCGTATGGTCCGTTTGG
CAATACCGGCGGTACCCCGTTTAGCCTGCCGATTGCCGCGGGTAAAATTAGC
GGCTTCTTTGGTCGTGGCGGTAAATTTCTGGATGCCATTGGCGTGTATCTGGA
ACCGCTCGAGTGA

>H84M (SEQ ID NO:6)
ATGAATGGTGCGATCAAAGTTGGCGCGTGGGGTGGCAACGGTGGTAGCGCCT
TTGATATGGGCCCGGCGTATCGTATTATTAGCGTGAAAATTTTTAGCGGTGAT
GTGGTTGATGGCGTTGATGTGACCTTTACCTATTATGGTAAAACCGAAACCCG
TCATTATGGCGGTAGCGGTGGTACCCCGCATGAAATTGTGCTGCAGGAAGGT
GAATATCTGGTGGGTATGGCGGGCGAAGTGGCGAACTATATGGGTGCGGTGG
TGCTGGGTAAACTGGGTTTTAGCACCAATAAAAAAGCGTATGGTCCGTTTGG
CAATACCGGCGGTACCCCGTTTAGCCTGCCGATTGCCGCGGGTAAAATTAGC
GGCTTCTTTGGTCGTGGCGGTAAATTTCTGGATGCCATTGGCGTGTATCTGGA
ACCGCTCGAGTGA

>Y83V (SEQ ID NO:7)
MNGAIKVGAWGGNGGSAFDMGPAYRIISVKIFSGDVVDGVDVTFTYYGKTETR
HYGGSGGTPHEIVLQEGEYLVGMAGEVANVHGAVVLGKLGFSTNKKAYGPFGN
TGGTPFSLPIAAGKISGFFGRGGKFLDAIGVYLEPLE

> Y83V (SEQ ID NO:8)
ATGAATGGTGCGATCAAAGTTGGCGCGTGGGGTGGCAACGGTGGTAGCGCCT
TTGATATGGGCCCGGCGTATCGTATTATTAGCGTGAAAATTTTTAGCGGTGAT
GTGGTTGATGGCGTTGATGTGACCTTTACCTATTATGGTAAAACCGAAACCCG
TCATTATGGCGGTAGCGGTGGTACCCCGCATGAAATTGTGCTGCAGGAAGGT

GAATATCTGGTGGGTATGGCGGGCGAAGTGGCGAACGTTCACGGTGCGGTGG

FIGURE 9 (cont.)

TGCTGGGTAAACTGGGTTTTAGCACCAATAAAAAAGCGTATGGTCCGTTTGG

CAATACCGGCGGTACCCCGTTTAGCCTGCCGATTGCCGCGGGTAAAATTAGC
GGCTTCTTTGGTCGTGGCGGTAAATTTCTGGATGCCATTGGCGTGTATCTGGA
ACCGCTCGAGTGA

SEQUENCE LISTING

<160> NUMBER OF SEQ ID NOS: 8

<210> SEQ ID NO 1
<211> LENGTH: 143
<212> TYPE: PRT
<213> ORGANISM: Artificial Sequence
<220> FEATURE:
<223> OTHER INFORMATION: Synthetic

<400> SEQUENCE: 1

```
Met Asn Gly Ala Ile Lys Val Gly Ala Trp Gly Gly Asn Gly Gly Ser
1               5                   10                  15

Ala Phe Asp Met Gly Pro Ala Tyr Arg Ile Ile Ser Val Lys Ile Phe
            20                  25                  30

Ser Gly Asp Val Val Asp Gly Val Asp Val Thr Phe Thr Tyr Tyr Gly
        35                  40                  45

Lys Thr Glu Thr Arg His Tyr Gly Gly Ser Gly Gly Thr Pro His Glu
    50                  55                  60

Ile Val Leu Gln Glu Gly Glu Tyr Leu Val Gly Met Ala Gly Glu Val
65                  70                  75                  80

Ala Asn Tyr Thr Gly Ala Val Val Leu Gly Lys Leu Gly Phe Ser Thr
                85                  90                  95

Asn Lys Lys Ala Tyr Gly Pro Phe Gly Asn Thr Gly Gly Thr Pro Phe
            100                 105                 110

Ser Leu Pro Ile Ala Ala Gly Lys Ile Ser Gly Phe Phe Gly Arg Gly
```

```
                115                 120                 125
Gly Lys Phe Leu Asp Ala Ile Gly Val Tyr Leu Glu Pro Leu Glu
    130                 135                 140

<210> SEQ ID NO 2
<211> LENGTH: 143
<212> TYPE: PRT
<213> ORGANISM: Artificial Sequence
<220> FEATURE:
<223> OTHER INFORMATION: Synthetic

<400> SEQUENCE: 2

Met Asn Gly Ala Ile Lys Val Gly Ala Trp Gly Gly Asn Gly Ser
1               5                   10                  15

Ala Phe Asp Met Gly Pro Ala Tyr Arg Ile Ile Ser Val Lys Ile Phe
                20                  25                  30

Ser Gly Asp Val Val Asp Gly Val Asp Val Thr Phe Thr Tyr Tyr Gly
            35                  40                  45

Lys Thr Glu Thr Arg His Tyr Gly Gly Ser Gly Gly Thr Pro His Glu
    50                  55                  60

Ile Val Leu Gln Glu Gly Glu Tyr Leu Val Gly Met Ala Gly Glu Val
65                  70                  75                  80

Ala Asn Tyr Ser Gly Ala Val Val Leu Gly Lys Leu Gly Phe Ser Thr
                85                  90                  95

Asn Lys Lys Ala Tyr Gly Pro Phe Gly Asn Thr Gly Gly Thr Pro Phe
            100                 105                 110

Ser Leu Pro Ile Ala Ala Gly Lys Ile Ser Gly Phe Phe Gly Arg Gly
        115                 120                 125

Gly Lys Phe Leu Asp Ala Ile Gly Val Tyr Leu Glu Pro Leu Glu
    130                 135                 140

<210> SEQ ID NO 3
<211> LENGTH: 143
<212> TYPE: PRT
<213> ORGANISM: Artificial Sequence
<220> FEATURE:
<223> OTHER INFORMATION: Synthetic

<400> SEQUENCE: 3

Met Asn Gly Ala Ile Lys Val Gly Ala Trp Gly Gly Asn Gly Ser
1               5                   10                  15

Ala Phe Asp Met Gly Pro Ala Tyr Arg Ile Ile Ser Val Lys Ile Phe
                20                  25                  30

Ser Gly Asp Val Val Asp Gly Val Asp Val Thr Phe Thr Tyr Tyr Gly
            35                  40                  45

Lys Thr Glu Thr Arg His Tyr Gly Gly Ser Gly Gly Thr Pro His Glu
    50                  55                  60

Ile Val Leu Gln Glu Gly Glu Tyr Leu Val Gly Met Ala Gly Glu Val
65                  70                  75                  80

Ala Asn Tyr Met Gly Ala Val Val Leu Gly Lys Leu Gly Phe Ser Thr
                85                  90                  95

Asn Lys Lys Ala Tyr Gly Pro Phe Gly Asn Thr Gly Gly Thr Pro Phe
            100                 105                 110

Ser Leu Pro Ile Ala Ala Gly Lys Ile Ser Gly Phe Phe Gly Arg Gly
        115                 120                 125

Gly Lys Phe Leu Asp Ala Ile Gly Val Tyr Leu Glu Pro Leu Glu
    130                 135                 140
```

<210> SEQ ID NO 4
<211> LENGTH: 432
<212> TYPE: DNA
<213> ORGANISM: Artificial Sequence
<220> FEATURE:
<223> OTHER INFORMATION: Synthetic

<400> SEQUENCE: 4

| | | | | | | |
|---|---|---|---|---|---|---|
| atgaatggtg | cgatcaaagt | tggcgcgtgg | ggtggcaacg | gtggtagcgc | ctttgatatg | 60 |
| ggcccggcgt | atcgtattat | tagcgtgaaa | attttagcg | gtgatgtggt | tgatggcgtt | 120 |
| gatgtgacct | ttacctatta | tggtaaaacc | gaaacccgtc | attatggcgg | tagcggtggt | 180 |
| accccgcatg | aaattgtgct | gcaggaaggt | gaatatctgg | tgggtatggc | gggcgaagtg | 240 |
| gcgaactata | ctggtgcggt | ggtgctgggt | aaactgggtt | ttagcaccaa | taaaaaagcg | 300 |
| tatggtccgt | ttggcaatac | cggcggtacc | ccgtttagcc | tgccgattgc | cgcgggtaaa | 360 |
| attagcggct | tctttggtcg | tggcggtaaa | tttctggatg | ccattggcgt | gtatctggaa | 420 |
| ccgctcgagt | ga | | | | | 432 |

<210> SEQ ID NO 5
<211> LENGTH: 432
<212> TYPE: DNA
<213> ORGANISM: Artificial Sequence
<220> FEATURE:
<223> OTHER INFORMATION: Synthetic

<400> SEQUENCE: 5

| | | | | | | |
|---|---|---|---|---|---|---|
| atgaatggtg | cgatcaaagt | tggcgcgtgg | ggtggcaacg | gtggtagcgc | ctttgatatg | 60 |
| ggcccggcgt | atcgtattat | tagcgtgaaa | attttagcg | gtgatgtggt | tgatggcgtt | 120 |
| gatgtgacct | ttacctatta | tggtaaaacc | gaaacccgtc | attatggcgg | tagcggtggt | 180 |
| accccgcatg | aaattgtgct | gcaggaaggt | gaatatctgg | tgggtatggc | gggcgaagtg | 240 |
| gcgaactata | gtggtgcggt | ggtgctgggt | aaactgggtt | ttagcaccaa | taaaaaagcg | 300 |
| tatggtccgt | ttggcaatac | cggcggtacc | ccgtttagcc | tgccgattgc | cgcgggtaaa | 360 |
| attagcggct | tctttggtcg | tggcggtaaa | tttctggatg | ccattggcgt | gtatctggaa | 420 |
| ccgctcgagt | ga | | | | | 432 |

<210> SEQ ID NO 6
<211> LENGTH: 432
<212> TYPE: DNA
<213> ORGANISM: Artificial Sequence
<220> FEATURE:
<223> OTHER INFORMATION: Synthetic

<400> SEQUENCE: 6

| | | | | | | |
|---|---|---|---|---|---|---|
| atgaatggtg | cgatcaaagt | tggcgcgtgg | ggtggcaacg | gtggtagcgc | ctttgatatg | 60 |
| ggcccggcgt | atcgtattat | tagcgtgaaa | attttagcg | gtgatgtggt | tgatggcgtt | 120 |
| gatgtgacct | ttacctatta | tggtaaaacc | gaaacccgtc | attatggcgg | tagcggtggt | 180 |
| accccgcatg | aaattgtgct | gcaggaaggt | gaatatctgg | tgggtatggc | gggcgaagtg | 240 |
| gcgaactata | tggtgcggt | ggtgctgggt | aaactgggtt | ttagcaccaa | taaaaaagcg | 300 |
| tatggtccgt | ttggcaatac | cggcggtacc | ccgtttagcc | tgccgattgc | cgcgggtaaa | 360 |
| attagcggct | tctttggtcg | tggcggtaaa | tttctggatg | ccattggcgt | gtatctggaa | 420 |
| ccgctcgagt | ga | | | | | 432 |

-continued

```
<210> SEQ ID NO 7
<211> LENGTH: 143
<212> TYPE: PRT
<213> ORGANISM: Artificial Sequence
<220> FEATURE:
<223> OTHER INFORMATION: Synthetic

<400> SEQUENCE: 7

Met Asn Gly Ala Ile Lys Val Gly Ala Trp Gly Gly Asn Gly Gly Ser
1               5                   10                  15

Ala Phe Asp Met Gly Pro Ala Tyr Arg Ile Ile Ser Val Lys Ile Phe
            20                  25                  30

Ser Gly Asp Val Val Asp Gly Val Asp Val Thr Phe Thr Tyr Tyr Gly
        35                  40                  45

Lys Thr Glu Thr Arg His Tyr Gly Gly Ser Gly Gly Thr Pro His Glu
    50                  55                  60

Ile Val Leu Gln Glu Gly Glu Tyr Leu Val Gly Met Ala Gly Glu Val
65                  70                  75                  80

Ala Asn Val His Gly Ala Val Val Leu Gly Lys Leu Gly Phe Ser Thr
                85                  90                  95

Asn Lys Lys Ala Tyr Gly Pro Phe Gly Asn Thr Gly Gly Thr Pro Phe
            100                 105                 110

Ser Leu Pro Ile Ala Ala Gly Lys Ile Ser Gly Phe Phe Gly Arg Gly
        115                 120                 125

Gly Lys Phe Leu Asp Ala Ile Gly Val Tyr Leu Glu Pro Leu Glu
    130                 135                 140

<210> SEQ ID NO 8
<211> LENGTH: 432
<212> TYPE: DNA
<213> ORGANISM: Artificial Sequence
<220> FEATURE:
<223> OTHER INFORMATION: Synthetic

<400> SEQUENCE: 8
atgaatggtg cgatcaaagt tggcgcgtgg ggtggcaacg gtggtagcgc ctttgatatg      60
ggcccggcgt atcgtattat tagcgtgaaa atttttagcg gtgatgtggt tgatggcgtt     120
gatgtgacct ttacctatta tggtaaaacc gaaacccgtc attatggcgg tagcggtggt     180
accccgcatg aaattgtgct gcaggaaggt gaatatctgg tgggtatggc gggcgaagtg     240
gcgaacgttc acggtgcggt ggtgctgggt aaactgggtt ttagcaccaa taaaaaagcg     300
tatggtccgt ttggcaatac cggcggtacc ccgtttagcc tgccgattgc cgcgggtaaa     360
attagcggct tctttggtcg tggcggtaaa tttctggatg ccattggcgt gtatctggaa     420
ccgctcgagt ga                                                         432
```

LECTINS AND USES THEREOF

This application is a national phase application under 35 U.S.C. §371 of PCT International Application No. PCT/US2011/031895, filed on Apr. 11, 2011, which claims priority to provisional application 61/324,107, filed Apr. 14, 2010, each of which are herein incorporated by reference in its entirety.

STATEMENT REGARDING FEDERALLY SPONSORED RESEARCH OR DEVELOPMENT

This invention was made with government support under AI062248 awarded by the National Institutes of Health. The government has certain rights in the invention.

FIELD OF THE INVENTION

The present invention relates to chemical compounds, methods for their discovery, and their therapeutic and research use. In particular, the present invention provides antiviral and antimicrobial lectin compounds and methods of their use.

BACKGROUND OF THE INVENTION

Acquired immune deficiency syndrome or acquired immunodeficiency syndrome (AIDS or Aids) is a collection of symptoms and infections resulting from the specific damage to the immune system caused by the human immunodeficiency virus (HIV) in humans (see, e.g., Marx, J. L. (1982) Science 217 (4560): 618-621; herein incorporated by reference in its entirety), and similar viruses in other species (SIV, FIV, etc.). The late stage of the condition leaves individuals prone to opportunistic infections and tumors. Although treatments for AIDS and HIV exist to slow the virus' progression, there is no known cure. HIV is transmitted through direct contact of a mucous membrane or the bloodstream with a bodily fluid containing HIV, such as blood, semen, vaginal fluid, preseminal fluid, and breast milk. This transmission can come in the form of anal, vaginal or oral sex, blood transfusion, contaminated hypodermic needles, exchange between mother and baby during pregnancy, childbirth, or breastfeeding, or other exposure to one of the above bodily fluids.

In the absence of antiretroviral therapy, the median time of progression from HIV infection to AIDS is nine to ten years, and the median survival time after developing AIDS is only 9.2 months (see, e.g., Morgan, et al., (2002) AIDS 16 (4): 597-632; herein incorporated by reference in its entirety). The use of highly active antiretroviral therapy prolongs both the median time of progression to AIDS and the median survival time.

There is currently no vaccine or cure for HIV or AIDS. The only known methods of prevention are based on avoiding exposure to the virus or, failing that, an antiretroviral treatment directly after a highly significant exposure, called post-exposure prophylaxis (PEP). PEP has a very demanding four week schedule of dosage. It also has very unpleasant side effects including diarrhea, malaise, nausea and fatigue. What is needed are improved methods for treating HIV and AIDS.

SUMMARY OF THE INVENTION

The present invention relates to chemical compounds, methods for their discovery, and their therapeutic and research use. In particular, the present invention provides antiviral and antimicrobial lectin compounds and methods of their use.

In some embodiments, the present invention provides antiviral lectin compounds with reduced or low mitogenicity and methods of their use. In some embodiments, the present invention provides a composition comprising a BanLec polypeptide (e.g., a variant BanLec polypeptide) (e.g., in isolated or purified form), wherein the BanLec polypeptide exhibits antiviral activity but exhibits reduced mitogenic activity relative to wild type BanLec (e.g., the mitogenic activity is reduced at least 10%, at least 20%, at least 50%, at least 75%, at least 85%, at least 90%, at least 95% etc) relative to wild type BanLec or other lectins). In some embodiments, the BanLec polypeptide is, for example, the polypeptide described by SEQ ID NOs:1-3 or is encoded by a nucleic acid described by SEQ ID NOs:4-6, or other suitable nucleic acid sequences. In some embodiments, the BanLec polypeptide comprises a mutation from wild-type at position 84. In some embodiments, histidine 84 is mutated, for example, to a threonine (H84T), serine (H84S), or methionine (H84M). In some embodiments, the BanLec polypeptide is, for example, the polypeptide described by SEQ ID NO:7 or is encoded by a nucleic acid described by SEQ ID NO:8, or other suitable nucleic acid sequence. In some embodiments, the BanLec polypeptide comprises a mutation from wild-type at position 83. In some embodiments, tyrosine 83 is mutated, for example, to a valine (Y83V). In some embodiments, a BanLec polypeptide comprises a Y83V mutation and one or more of H84T, H84S, and H84M.

In some embodiments, the present invention provides antiviral, antimicrobial, and/or antibiotic compositions. In some embodiments, compositions provided herein are systemic, local, topical, etc. (e.g., topical anti-viral composition). Embodiments of the present invention provide expression vectors (e.g., comprising a purification tag) comprising nucleic acids encoding BanLec polypeptides and host cells comprising the expression vectors. In some embodiments, the present invention provides a method of preventing infection by a virus (e.g., HIV), bacteria (e.g. *helobacter pilori*), and/or parasite (e.g., *Leshmania infantum*) comprising: contacting a surface suspected of comprising the virus, bacteria, or parasite with the aforementioned composition. In some embodiments, the present invention provides a method of treating a subject diagnosed with a viral infection (e.g., HIV), bacterial infection (e.g. *helobacter pilori*), and/or parasitic infection (e.g., *Leshmania infantum*) comprising: administering the aformentioned composition to the subject. In some embodiments, the present invention provides compositions and methods to treat or prevent infections of viruses including but not limited to: HIV, HCV, Dengue virus, Marburg virus, Ebola virus, West Nile virus, Cytomegalovirus, Herpes virus (e.g., type 8), Corona virus (e.g, SARS), and Measles virus. In some embodiments, the present invention provides compositions and methods to treat or prevent infections of bacteria including but not limited to: *Mycobacterium tuberculosis, Mycobacterium leprae, Mycobacteriumbovis, Streptococcus pneumoniae* (e.g., serotypes 3 and 14), *Helobacter pilori*, and *Lactobacillus* spp. In some embodiments, the present invention provides compositions and methods to treat or prevent infections of parasites including but not limited to: *Leshmania infantum, Leshmania pifanoi, Leshmania mexicana*, and *Schistosoma mansoni* parasite. In some embodiments, the present invention provides compositions and methods to treat or prevent infections of fungi including but not limited to: *Aspergillus fumigatus* and *Candida albicans*. In some embodiments, the present invention provides compositions and methods to treat or prevent infections by any microorganisms with mannose on their surfaces. In some embodiments, compositions of the present invention (e.g. BanLec and/or BanLec mutants) bind to mannose on the surface of microorganisms. In some embodiments, the present invention provides compositions and methods (e.g. BanLec and/or BanLec mutants) to treat or prevent infections by microorganisms that interact with the DC-SIGN receptor.

DESCRIPTION OF THE FIGURES

FIG. 1 shows mitogenic activity of H84T.

FIG. 2 shows mitogenic activity of mutants H84S, H84M, H84Y, and H84A.

FIG. 3 shows a comparison of the anti-HIV-1 activities of natural and recombinant BanLec. Natural BanLec isolated from the fruit of bananas or recombinant BanLec isolated from *E. coli* was added to TZM-b1 cells 30 minutes prior to infection with either the HIV-1 isolate YU2 (A) or 90CF402 (B). Forty-eight hours post viral incubation, infection was quantified by measuring luciferase activity. (C) Comparison of the mitogenic activity of BanLec to other lectins.

FIG. 4 shows properties of H84T. (A) Comparison of the mitogenic activity of H84T to rBanLec. (B) Induction of the activation marker CD69 on CD4 T cells in the presence of BanLec or H84T BanLec as measured by flow cytometry. (C) Induction of cytokines/chemokines by Banlec and H84T Banlec. (D) H84T retains anti-HIV-1 activity.

FIG. 5 shows expression of Recombinant BanLec. Coomassie-stained SDS-PAGE gel of the purification of recombinant BanLec. The gel lanes were loaded as follows: 1: Molecular weight marker 2: lysate containing recombinant BanLec 3: column load flow-through 4: 25 mM imidazole wash 5: first 250 mM imidazole elution 6: 2nd 250 mM imidazole elution 7: Banana-derived BanLec 8: lysozyme protein that was used for the cellular lysis step.

FIG. 6 shows that BanLec inhibits HIV-1 containing consensus subtype B and subtype C envelopes.

FIG. 7 shows a comparison of the three-dimensional crystal structures of BanLec and BanLec H84T.

FIG. 8 shows the difference in the structural motion of BanLec WT vs. H84T when bound to α-Methyl D-mannoside. Correlation of the peak intensities in the 1H-15N HSQC spectra of (A.) unbound BanLec (inset, overlay of WT and H84T) and (B.) in the presence of α-Methyl D-mannoside (inset, overlay of WT and H84T).

FIG. 9 shows sequences of variant BanLec peptides.

DEFINITIONS

To facilitate an understanding of the present invention, a number of terms and phrases are defined below.

As used herein, the term "subject" refers to organisms to be treated by the methods of embodiments of the present invention. Such organisms preferably include, but are not limited to, mammals (e.g., murines, simians, equines, bovines, porcines, canines, felines, and the like), and most preferably includes humans. In the context of the invention, the term "subject" generally refers to an individual who will receive or who has received treatment (e.g., administration of a peptide of the present invention and optionally one or more other agents) for a condition characterized by infection by a microorganism or risk of infection by a microorganism.

The term "diagnosed," as used herein, refers to the recognition of a disease by its signs and symptoms (e.g., resistance to conventional therapies), or genetic analysis, pathological analysis, histological analysis, diagnostic assay (e.g., for microorganism infection) and the like.

As used herein the term, "in vitro" refers to an artificial environment and to processes or reactions that occur within an artificial environment. In vitro environments include, but are not limited to, test tubes and cell cultures. The term "in vivo" refers to the natural environment (e.g., an animal or a cell) and to processes or reaction that occur within a natural environment.

As used herein, the term "host cell" refers to any eukaryotic or prokaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "effective amount" refers to the amount of a therapeutic agent (e.g., a peptide of the present invention) sufficient to effect beneficial or desired results. An effective amount can be administered in one or more administrations, applications or dosages and is not intended to be limited to a particular formulation or administration route.

As used herein, the term "co-administration" refers to the administration of at least two agent(s) (e.g., a peptide of the present invention) or therapies to a subject. In some embodiments, the co-administration of two or more agents/therapies is concurrent. In some embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "toxic" refers to any detrimental or harmful effects on a cell or tissue as compared to the same cell or tissue prior to the administration of the toxicant.

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

The term "sample" as used herein is used in its broadest sense. A sample may comprise a cell, tissue, or fluids, nucleic acids or polypeptides isolated from a cell (e.g., a microorganism), and the like.

As used herein, the terms "purified" or "to purify" refer, to the removal of undesired components from a sample. As used herein, the term "substantially purified" refers to molecules that are at least 60% free, preferably 75% free, and most preferably 90%, or more, free from other components with which they usually associated.

As used herein, the term "modulate" refers to the activity of a compound (e.g., a compound of the present invention) to affect (e.g., to kill or prevent the growth of) a microorganism.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "test compound" refers to any chemical entity, pharmaceutical, drug, and the like, that can be used to treat or prevent a disease, illness, sickness, or disorder of bodily function, or otherwise alter the physiological or cellular status of a sample (e.g., infection by a microorganism). Test compounds comprise both known and potential therapeutic compounds. A test compound can be determined to be therapeutic by using the screening methods of the present invention. A "known therapeutic compound" refers to a therapeutic compound that has been shown (e.g., through animal trials or prior experience with administration to humans) to be effective in such treatment or prevention. In some embodiments, "test compounds" are agents that treat or prevent infection by a microorganism.

DETAILED DESCRIPTION OF THE INVENTION

The present invention relates to chemical compounds, methods for their discovery, and their therapeutic and research use. In particular, the present invention provides antiviral and antimicrobial lectin compounds and methods of their use.

The lectin termed BanLec, isolated from the ripened fruit of the banana (*Musa acuminata* cultivars), exists as a dimer with a molecular mass of approximately 30 kDa. It is a member of the jacalinrelated lectin family and can recognize high mannose structures. Lectins in this family are characterized by the presence of β-prism 1 structure composed of three Greek Key turn motifs. Greek Keys 1 and 2 are both involved in binding carbohydrates and contain a GXXXD binding motif, whereas Key 3 does not contain the binding motif. However, this loop can assist ligand binding and determine lectin specificity.

BanLec possesses a variety of properties that make it appealing for development as a microbicide component, including high stability, broad anti-HIV activity, and ability to be produced in *E. coli*. In addition, BanLec is already is frequently consumed by numerous people, and this may result in oral tolerance as evident from reported IgG4 antibody responses (tolerogenic) to BanLec. BanLec has been shown to have therapeutic utility as a component of anti-HIV therapeutic or microbiocide (e.g., vaginal or rectal microbiocide). However, safety concerns exist regarding the mitogenic and inflammatory activities of lectins. Those concerns were addressed during the course of development of embodiments of the present invention by creating a BanLec variant, H84T, which retains anti-HIV-1 activity yet displays very markedly reduced mitogenic and pro-inflammatory activity.

BanLec is a potent inhibitor of HIV infection that markedly reduces the replication of a range of HIV-1 isolates (Swanson et al., J. Biol. Chem. 285:8646 (2010); herein incorporated by reference in its entirety). Experiments conducted during the course of development of embodiments of the present invention demonstrated BanLec activity.

Embodiments of the present invention provide modified BanLec sequences (e.g., SEQ ID NOs: 1-6) or active fragments thereof. The amino acid sequence of BanLec was altered to reduce its mitogenic activity while maintaining potent anti-HIV activity. Mutations were introduced into an expression vector containing a DNA sequence encoding for BanLec through the use of a commercially available site-directed mutagenesis kit. The mutations were confirmed by DNA sequencing, and the resulting mutants were expressed and purified. The purified mutants were then tested for mitogenic activity.

Accordingly, in some embodiments, the present invention provides lectins where the mitogenicity has been separated from the anti-HIV properties. The present invention is illustrated with the BanLec lectin. However, the present invention is not limited to BanLec. Embodiments of the present invention provide additional lectins (e.g., from other species) that have the mitogenecity reduced or eliminated while retaining useful therapeutic properties.

The present invention is not limited to the BanLec mutants described herein (e.g., SEQ ID NOs: 1-8). Any mutation that results in a reduction or decrease in mitogenicity while retaining anti-viral properties is contemplated to be within the scope of the present invention.

In some embodiments, the present invention provide variant BanLec polypeptides that exhibit reduced mitogentic activity relative to wild type BanLec (e.g., the mitogenic activity is reduced at least 10%, at least 20%, at least 50%, at least 75%, at least 85%, at least 90%, at least 95% etc) relative to wild type BanLec or other lectins.

The mutant BanLec lectins described herein find use in a variety of applications. For example, in some embodiments, non-mitogenic BanLec polypeptides (e.g., SEQ ID NOs: 1-3) find use in therapeutic compositions to treat viral infections (e.g., HIV). In some embodiments, non-mitogenic BanLec polypeptides are used in combinations with known HIV therapeutic agents (e.g., as part of a therapeutic cocktail). One of ordinary skill in the art knows well how to formulate such therapeutic cocktails.

In some embodiments, BanLec compositions (e.g., SEQ ID NOs: 1-3 and 7) are used as a component of topic antiviral compositions (e.g., to kill HIV and thus prevent infection). For example, in some embodiments, BanLec (e.g., those described by SEQ ID NOs: 1-3 and 7) are included in formulations for use as vaginal anti-viral agents (e.g., to be used prior to or following contact with bodily fluids (e.g., sperm) containing or suspected of containing HIV). In some embodiments, anti-viral formulations comprising BanLec are used to treat condoms, sex toys or other objects likely to contact bodily fluids containing HIV or other pathogenic viruses.

The present invention is not limited to the treatment or killing of HIV. As BanLec inhibits viral replication by binding to the sugars on viral envelopes, it finds use in the prevention or treatment of other viral infections of humans, animals, and plants. In some embodiments, compositions described herein are not limited to antiviral applications. In some embodiments, compositions find use as anti-microbial, anti-bacterial, anti-parasitic, and anti-fungal agents. For example, in some embodiments, the present invention provides compositions and methods to treat or prevent infections of viruses including but not limited to: HIV, HCV, Dengue virus, Marburg virus, Ebola virus, West Nile virus, Cytomegalovirus, Herpes virus (e.g., type 8), Corona virus (e.g., SARS), and Measles virus. In some embodiments, the present invention provides compositions and methods to treat or prevent infections of bacteria including but not limited to: *Mycobacterium tuberculosis, Mycobacterium leprae, Mycobacteriumbovis, Streptococcus pneumoniae* (e.g., serotypes 3 and 14), *Helobacter pilori*, and *Lactobacillus* spp. In some embodiments, the present invention provides compositions and methods to treat or prevent infections of parasites including but not limited to: *Leshmania infantum, Leshmania pifanoi, Leshmania mexicana,* and *Schistosoma mansoni* parasite. In some embodiments, the present invention provides compositions and methods to treat or prevent infections of fungi including but not limited to: *Aspergillus fumigatus* and *Candida albicans*.

In some embodiments, compositions find use in treating infections involving organisms presenting appropriate surface sugars (e.g., mannose). In some embodiments, compositions are not limited to surface application. In some embodiments, compositions are administrated by and suitable delivery route understood by those in the pharmaceutical field (e.g., intravenous, oral, topical, etc.).

Embodiments of the present invention further provide pharmaceutical compositions (e.g., comprising one or more of the therapeutic agents described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration (e.g., to tissues, wounds, organs, etc) may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the active agents of the formulation.

Dosing is dependent on severity and responsiveness of the disease state or condition to be treated, with the course of treatment lasting from several days to several months, or until a cure is effected or a diminution of the disease state is achieved. In some embodiments, treatment is administered in one or more courses, where each course comprises one or more doses per day for several days (e.g., 1, 2, 3, 4, 5, 6) or weeks (e.g., 1, 2, or 3 weeks, etc.). In some embodiments, courses of treatment are administered sequentially (e.g., without a break between courses), while in other embodiments, a break of 1 or more days, weeks, or months is provided between courses. In some embodiments, treatment is provided on an ongoing or maintenance basis (e.g., multiple courses provided with or without breaks for an indefinite time period). Optimal dosing schedules can be calculated from measurements of drug accumulation in the body of the patient. The administering physician can readily determine optimum dosages, dosing methodologies and repetition rates.

In some embodiments, dosage is from 0.01 μg to 100 g per kg of body weight, and may be given once or more daily, weekly, monthly or yearly. The treating physician can estimate repetition rates for dosing based on measured residence times and concentrations of the drug in bodily fluids or tissues.

EXPERIMENTAL

The following examples are provided in order to demonstrate and further illustrate certain preferred embodiments and aspects of the present invention and are not to be construed as limiting the scope thereof.

Example 1

To determine the anti-HIV activity of BanLec, different concentrations of the lectin were incubated with TZM-b1 indicator cells before infection with various HIV-1 isolates. The ability of BanLec to inhibit several different HIV-1 isolates was investigated. The viral clones 81A-4 and NL(AD8) are both derivatives of NL4-3 in which a portion of the envelope is swapped with the envelope region from either the R5 HIV-1 isolates BaL or ADA, respectively. 81A-4 and NL(AD8) use CCR5 as a cellular co-receptor (R5 tropic), whereas NL4-3 uses CXCR4 (X4 tropic). These isolates allow for the assessment of different HIV-1 envelope sensitivity to BanLec while keeping the remainder of the NL4-3 viral components unchanged. The dual-tropic isolate 89.6 was also assessed for susceptibility to BanLec. Dose-dependent inhibition of viral infection with $IC_{50}$ values calculated in the low nanomolar range against viral isolates with different tropisms were observed.

The anti-HIV activity of BanLec was further confirmed with the HIV-1 indicator cell line, MAGI-CCR5. With this cell line, the ability of BanLec to inhibit infection by the laboratory-adapted isolates BaL (R5) and Bru (X4) and the primary isolates ASM 44 (R5X4) and ASM 54 (R5X4) was assayed and it was determined that all were inhibited by BanLec.

R5 tropic viruses are the dominant form found in sexually transmitted HIV-1. To determine whether BanLec could inhibit additional primary isolates from different clades, BanLec was tested for inhibition of HIV-1 pseudotyped with envelopes derived from primary isolates of subtypes B and C. These subtypes are commonly found in North and Central America (subtype B) and parts of Africa and India (subtype C). Potent, subnanomolar inhibition of viral replication by BanLec was observed.

Macrophages are susceptible to HIV-1 infection and can become viral reservoirs that cannot be eliminated by highly active antiretroviral therapy. The role of vaginal macrophages in HIV-1 pathogenesis has not been fully characterized, but recent evidence indicates that these cells are permissive for HIV-1 infection. The ability of BanLec to inhibit HIV-1 infection of MDM was assayed. Nanomolar concentrations of BanLec inhibited HIV replication in MDM over a period of 15 days. Furthermore, BanLec had no effect on cellular viability as determined by MTT assay performed on day 15; therefore, this effect was not due to cellular toxicity. When BanLec remained in the culture supernatant for 7 days without changing the media or adding additional lectin, the $IC_{50}$ value for BanLec inhibition of HIV-1 replication was 9.72 nM, demonstrating that BanLec remains a potent and stable inhibitor in a long term culture system at 37° C.

The ability of BanLec to block cellular entry of HIV-1 in PBL was tested. It was contemplated that BanLec binds to high mannose structures found on the HIV-1 envelope, preventing entry and, thus, infection. If so, little or none of the strong-stop DNA product of early HIV-1 reverse transcription should be detected when cells are exposed to HIV-1 in the presence of BanLec. PBL were incubated with the HIV-1 Bru isolate in the presence of different concentrations of BanLec. As a positive control and for comparison, a similar experiment with the lectin GNA was performed in parallel. Real-time PCR was used to detect strong-stop DNA, which is a reverse transcription product that can be detected early after viral entry before viral uncoating takes place. Strong-stop DNA that may have been present in the virus stock was removed by treatment with DNase I to eliminate false detection of reverse transcription products. Treatment with BanLec resulted in a marked decrease in strong-stop DNA at low lectin concentrations indicating that, in addition to inhibiting viral replication in MDM, BanLec blocks HIV-1 infection in PBL. Furthermore, this inhibition occurs at a step before early replication events, at the level of viral entry.

BanLec is known to bind to mannose, and thus, it was hypothesized that BanLec binds the high mannose structures found on the glycosylated gp120 envelope protein and blocks entry of HIV-1 into cells. A BanLec-based ELISA was used to measure binding of glycosylated HIV-1 gp120 to BanLec. It was observed that BanLec binds to gp120 in a concentration-dependent manner. Furthermore, a known BanLec ligand, methyl-α-D mannopyranoside, inhibited such binding in a concentration dependent manner A high concentration of methyl-α-D-mannopyranoside ligand was needed to compete for binding to gp120 because of the high density of carbohydrate residues on the HIV-1 envelope protein. The ability of BanLec to block binding by the monoclonal antibody 2G12 was determined using the ELISA-based assay. 2G12 recognizes a cluster of N-linked glycosylation structures at positions Asn-295, -332, and -392 (position numbering is of the HXB2 reference sequence) that are crucial for antibody recognition. It was found that pretreatment of gp120 with BanLec inhibited recognition by 2G12 in a dose-dependent manner, indicating that BanLec is capable of binding to this antibody's epitope consisting of high mannose structures.

To further investigate at which point in the viral life cycle BanLec inhibits HIV-1 infection, it was tested BanLec for its ability to inhibit HIV-1 infection post-attachment. To do so, it was tested if BanLec could inhibit HIV-1 that was already bound to the cell but could not complete fusion due to temperature restriction. A large decrease in the inhibitory activity of the HIV-1 attachment inhibitor CD4-IgG2 in the post-attachment assay was observed, whereas the bound virus was still essentially completely susceptible to the fusion inhibitor T-20. This demonstrated that viral attachment, but not fusion, took place at 16° C. Both the CCR5 binding inhibitor maraviroc and BanLec primarily blocked viral replication by inhibiting HIV-1 attachment, but each has a modest effect on viral fusion.

The amino acid sequence of BanLec was altered to reduce its mitogenic activity while maintaining potent anti-HIV activity. Mutations were introduced into an expression vector containing a DNA sequence encoding for BanLec through the use of a commercially available site-directed mutagenesis kit. The mutations were confirmed by DNA sequencing, and the resulting mutants were expressed and purified. The purified mutants were then tested for mitogenic activity.

Mutants were also tested for anti-HIV activity and were compared to the activity of the wild-type form. TZM-b1 cells were pretreated with different concentrations of wild-type or mutant forms of BanLec prior to infection with pseudotyped HIV-1 containing a consensus subtype C envelope. Infection was quantified by measuring the reporter gene activity that is produced in response to infection. $IC_{50}$ values of the mutant and wild-type sequences were determined by non-linear regression. The fold decrease in anti-HIV activity of a mutant was determined by dividing the $IC_{50}$ value of the mutant by the $IC_{50}$ of the wild-type BanLec protein.

Figure 2:
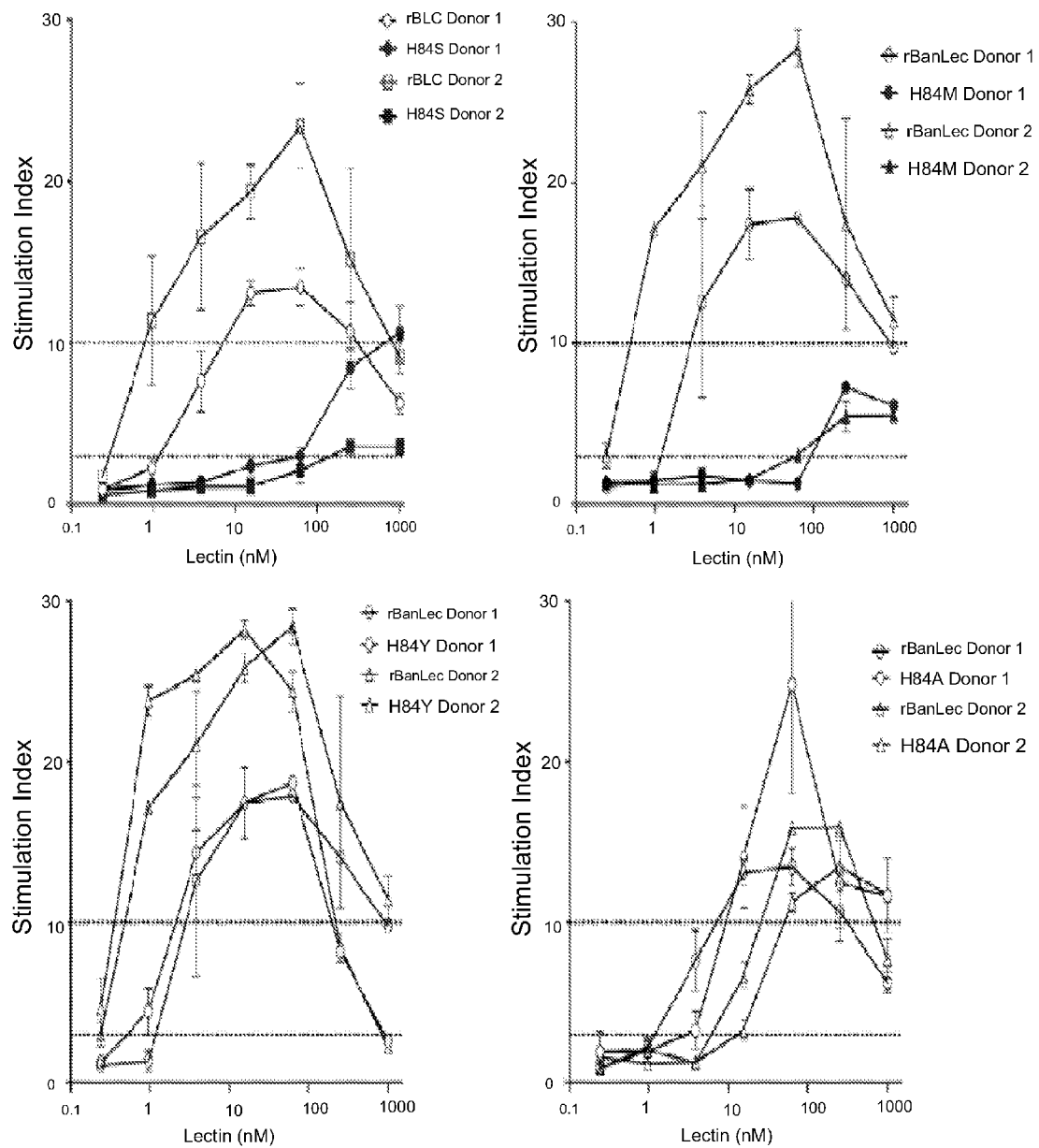

A reduction in the mitogenic activity was achieved by mutation of the amino acid histidine at position 84 of BanLec to the amino acids, threonine (H84T), serine (H84S), or methionine (H84M) (FIGS. 1 & 2). Not all mutations lead to this phenotype; substitution of histidine 84 with an alanine (H84A) or tyrosine (H84Y) does not lead to a decrease in mitogenic activity. The mutants H84T, H84S, and H84M had a decrease in anti-HIV activity, but they retain potent $IC_{50}$ values in the nanomolar range. In addition, the fold decrease in anti-HIV activity is much smaller than the decrease in mitogenic activity (table 1).

FIG. 1 shows mitogenic activity of H84T. Mitogenic activity was assessed by measuring the proliferation of peripheral blood lymphocytes (PBL). PBL were isolated from healthy donors. The cells were incubated with different concentrations of lectin or PBS as a control. The cells were incubated for three days and then BrdU was added to the culture. Proliferating cells incorporated the BrdU and was then quantified by an anti-BrdU ELISA. For quantification, mitogenic activity is expressed as stimulation index. This is the value for the treated sample divided by the PBS treated control. Typically a lectin is considered to be mitogenic if the stimulation index is greater than three, the lower hashed line. However, values for griffithsin exceeding three were observed. Since this has been reported to be non-mitogenic the ten was used as a cut-off since griffithsin did not exceed this threshold in all but one case. rBanLec represents cloned, wild-type BanLec while H84T represents cloned BanLec in which histidine 84 has been changed to a threonine.

FIG. 2 shows mitogenic activity of mutants H84S, H84M, H84Y, and H84A. Mitogenic activity was assessed as described in FIG. 1. rBanLec represents cloned, wild-type BanLec while H84S, H84M, H84Y, and H84A represents cloned BanLec in which histidine 84 has been changed to a serine, methionine, tyrosine, or alanine respectively. Table 1 provides a summary of antiviral activity and mitogenic activity of exemplary BanLec mutants.

TABLE 1

Summary of anti-HIV and mitogenic activity of BanLec mutants.

| BanLec Mutant | $IC_{50}$(nM) | Fold Decrease in Anti-HIV activity | Fold decrease in mitogenic activity as compared to wild-type BanLec. Values are for individual donors. |
|---|---|---|---|
| H84T | 7.0 | 23 | 256 |
| | | | 1031 |
| | | | 4167 |
| H84S | 1.6 | 4.1 | 4167 |
| | | | 64 |
| H84M | 7.7 | 21 | 4167 |
| | | | 1031 |
| H84A | 0.7 | 2.5 | 1 |
| | | | 1 |
| H84Y | 0.29 | No decrease | 1 |
| | | | 1 |

Example 2

Methods

Lectins and Carbohydrates

Methyl-α-D-mannopyranoside and PHA-L lectin were obtained from Sigma. The lectin GRFT was obtained from the NIH AIDS Reagent and Reference Program. The lectins GNA and BanLec were isolated through previously described methods (Van Damme et al., FEBS Letters, 1987. 215(1): p. 140-144). Isolation of BanLec from *E. coli* is described below.

Construction and Mutation of BanLec Expression Vectors

A cDNA encoding a codon-optimized BanLec for expression in *E. coli* was generated for the protein sequence gi71042661 by Genscript. The cDNA was then cloned into the *E. coli* expression vector pET24b (Novagen) to be in frame with the 6×His tag. Site-directed mutations were introduced by the QuikChange Multi Site-Directed Mutagenesis Kit or by the QuikChange Lightning Multi Site-Directed Mutagenesis Kit (Stratagene). PCR primers for introduction of the desired mutations were designed using the QuikChange Primer Design Program.

Purification of Recombinant BanLec and Mutants

A plasmid containing either the wild-type or a mutant form of BanLec was used to transform MDS 42 T7 or RosettaBlue pLysS *E. coil* cells. An overnight culture was used to inoculate 2×YT media. When the $OD_{600}$ nm of the culture reached 0.7-1.0, protein expression was induced with IPTG at a final concentration of 1mM. Five hours post induction, the cultures were harvested and the cell pellets were frozen at −20° C. until further processing. Recombinant protein was isolated by resuspending the pellet in 5 ml of 50 mM Tris, 0.5 M NaCl, and 0.02% $NaN_3$ pH 8.0 (the buffers will be referred to hereafter as IMAC-#, where # represents the amount of imidazole in mM) per 100 ml of culture grown. Lysozyme and DNAse I were added at concentrations of 1 mg/ml and 5 μg/ml, respectively. The mixture was incubated at room temperature for 30 minutes with constant stirring. After the incubation, an equal volume of IMAC-50 buffer was added and the mixture was chilled on ice. Cells were further lysed with four rounds of 30 seconds of pulsed sonication at the 50% duty at power level 5 while on ice followed by a one minute rest period between each 30 seconds of sonication. The insoluble material was pelletted by centrifugation at 10,000×g for 20 minutes.

The resulting cleared lysate was added to Ni-NTA agarose (Qiagen) that had been equilibrated with IMAC-25 buffer. The lysate and the resin were incubated for one hour at 4° C. with orbital rotation. The column was returned to room temperature and the lysate was allowed to pass through the column via gravity. The column was then washed with IMAC-25 buffer until the flow-through had an absorbance value at $280_{nm}$ less than 0.05 (approximately 20 volumes; this would vary with the size of the column and flow rates). Elution of the protein was then performed with IMAC-250 buffer. The protein was then dialyzed against PBS using Slide-alyzer dialysis cassettes with a 10 kDa molecular weight cutoff (Pierce). Two two-hour dialysis procedures were performed at 4° C. against a volume greater than 200 times that of protein sample followed by overnight dialysis. The protein was then sterile-filtered through a 0.22 μm filter. The protein was aliquoted and stored at −80° C. prior to use, where it could then be stored again at 4° C. for short-term use. Protein was quantified by BCA (Pierce) using bovine serum albumin protein as a standard. FIG. 5 shows expression of recombinant BanLec.

Assessment of Anti-HIV Activity

To each well of a white 96-well plate, 100 μl of TZM-b1 cells resuspended at $1\times10^5$ cells/ml in DMEM media with 25 mM HEPES and 10% FBS were added to each well of a 96-well plate. The next day, the media was removed by aspiration and fresh media containing lectin or PBS as a control was added to the plate at a concentration two times more than the final concentration. After 30 minutes of incubation, virus diluted with media was added and the cells were incubated for 48 hours at 37° C. After the incubation, 100 μl of media were removed and replaced with 100 μl of One-Glo reagent (Promega) for determination of luciferase expression.

Virus Production

Virus was produced using previously described methods. Briefly, production of pseudotyped virus was performed by co-transfecting 293FT cells with a plasmid containing a proviral genome with a deletion in the envelope gene along with a plasmid that expresses an HIV-1 envelope gene. The following morning, the media was changed. Forty-eight hours post transfection, the supernatant was collected and centrifuged at approximately 300×g for 5 minutes to remove any contaminating cells. For NL4-3 virus production, 293FT cells were transfected with the pNL4-3 plasmid. Virus was harvested as described above. The viruses were quantified by determining titers with TZM-b1 cells or by measuring p24 antigen by ELISA.

Hemagglutination Assay

The hemagglutinating activity of the lectin was determined by a 2-fold serial dilution procedure using formaldehyde-treated rabbit erythrocytes as described previously (Nowak and Barondes, 393(1): p. 115-23; Mo et al., J Biol Chem, 2000. 275(14): p. 10623-9). The hemagglutination titer was defined as the reciprocal of the highest dilution still exhibiting hemagglutination.

Isothermal Titration Calorimetry

Binding constants of mutants for methyl-α-mannoside were determined by isothermal titration calorimetry using a MicroCal VP-ITC calorimeter (Micro-Cal, Northampton, Mass., USA) at 25° C. Data were analyzed using Origins Ver. 7 software supplied with the instrument. The lectin in PBS, generally at approx. 0.2 mM in subunits, was titrated with the ligand at 20 mM in the same buffer. The titration volumes were adjusted so that the titration proceeded to at least a 10-fold molar excess of ligand over lectin monomers. The relatively low binding constants ($K_a < 1000$ $M^{-1}$) precluded obtaining full saturation or a definite sigmoidal titration curve from which a definitive stoichiometry can be obtained; thus the stoichiometry was fixed at 1 for curve-fitting to determine Ka; values between about 0.5 and 2-3 had little effect on the Ka value obtained.

Assessment of Mitogenic Activity by BrdU Incorporation

PBLs were isolated as previously described, and resuspended in IMDM media containing 10% FBS (IMDM-10) at a concentration of $2 \times 10^6$ cells/ml (Swanson, et al., J Biol Chem, 2010. 285(12): p. 8646-55). 50 µl of cells were added per well of a white 96-well plate followed by 50 µl of IMDM-10 containing lectin at various concentrations or PBS. The cells were incubated at 37° C. for 3 days prior to an 18 hour addition of BrdU. Proliferation was measured by BrdU incorporation, which was detected via a chemiluminescent-ELISA (Cell Proliferation ELISA (chemiluminescent), Roche) as per the manufacturer's instructions. Mitogenic activity was quantified as a stimulation index, which is the signal of the stimulated cells divided by the signal of the non-treated cells (RLU of treated PBL/RLU of untreated PBL).

Flow Cytometry to Measure Cellular Activation

The expression of cellular activation markers was measured after a 3 day incubation of PBMCs with varying concentrations of MVN or CV—N at 37° C. Briefly, after washing with PBS containing 2% FBS, cells were incubated with FITC-conjugated anti-CD4 mAb in combination with PE-conjugated anti-CD25, anti-CD69, or anti-HLA-DR mAbs for 30 min at 4° C. For aspecific background staining, cells were stained in parallel with Simultest Control IgG γ1/γ2a (BD Biosciences). Finally, the cells were washed, fixed with 1% formaldehyde solution, and analyzed with a FACSCalibur, and data were acquired with CellQuest software and analyzed with the FLOWJO software.

Bio-Plex Cytokine Assay

PBMCs were cultured in the presence of several concentrations of lectin and culture supernatant was collected after 72 h. The cytokine production profile was determined by the Bio-Plex 200 system (Bio-Rad, Hercules, Calif.) and Bio-Plex Human Cytokine 27-plex assay according to the manufacturer's instructions. The 27-plex assay kit contains beads conjugated with mAbs specific for Interleukin-1α (IL-1a), IL-1ra, IL-2, IL-4, IL-5, IL-6, IL-7, IL-8, IL-9, IL-10, IL-12, IL-13, IL-15, IL-17, eotaxin, fibroblast growth factor (FGF), granulocyte colony-stimulating factor (G-CSF), granulocyte-macrophage-CSF (GM-CSF), interferon-γ (IFN-γ), interferon-inducible protein-10 (IP-10), monocyte chemoattractant protein-1 (MCP-1), macrophage inflammatory protein-1α (MIP-α), MIP-1β, platelet-derived growth factor-BB (PDGF-BB), regulated on activation normal T-cell expressed and secreted (RANTES), tumor necrosis factor-α (TNF-α), and vascular endothelial growth factor (VEGF). For each cytokine, nine standards ranging from 0.5 to 32,000 pg/ml were constructed and the minimum detectable dose was between 0.5-5 pg/ml. Standard curves and the concentrations of the cytokines within the samples were generated with the Bio-Plex Manager 4.1 software.

Statistical Analysis $IC_{50}$ values of HIV-1 inhibition by BanLec and variants were calculated using non-linear regression analysis found in Graph Pad Prism 5.0 software. Using previously reported structures of BanLec, amino acids that could potentially influence the lectin's binding activity were identified. BanLec has a β-I prism structure that is common to members of the JRL family (Meagher, J. L., et al., Glycobiology, 2005. 15(10): p. 1033-42; Singh, D. D., et al., Glycobiology, 2005, 15(10): p. 1025-32). This protein conformation consists of three Greek key structures, which are made up of β-strands. Particular amino acid loops found in the Greek keys play a role in carbohydrate binding. The first and second Greek keys include the JRL consensus binding motif: GXXXD. When mutations were introduced into the first and second Greek keys that eliminated mitogenicity, they also resulted in loss of almost all anti-HIV activity. The third Greek key varies among JRL members in terms of length and composition, and is also thought to play a role in carbohydrate specificity of larger carbohydrates ligands (Jeyaprakash, A. A., et al., J Mol Biol, 2004. 338(4): p. 757-70; Nakamura-Tsuruta, S., et al., Febs J, 2008. 275(6): p. 1227-39). The histidine at position 84 of BanLec is found in this third loop, and has been predicted to play a role in the binding of oligosaccharides (Singh et al., supra).

RESULTS

Figure 3:
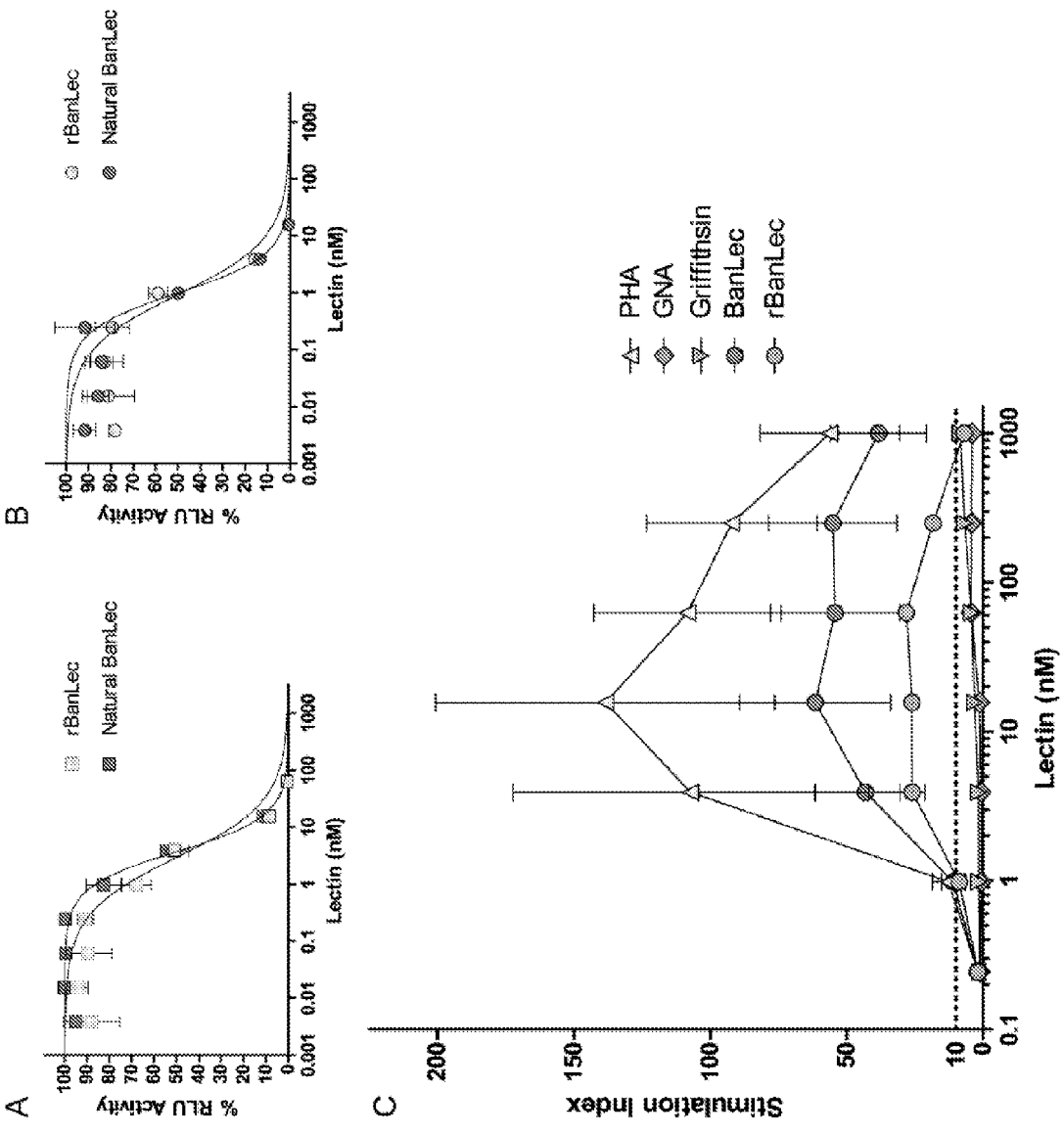
Figure 4:
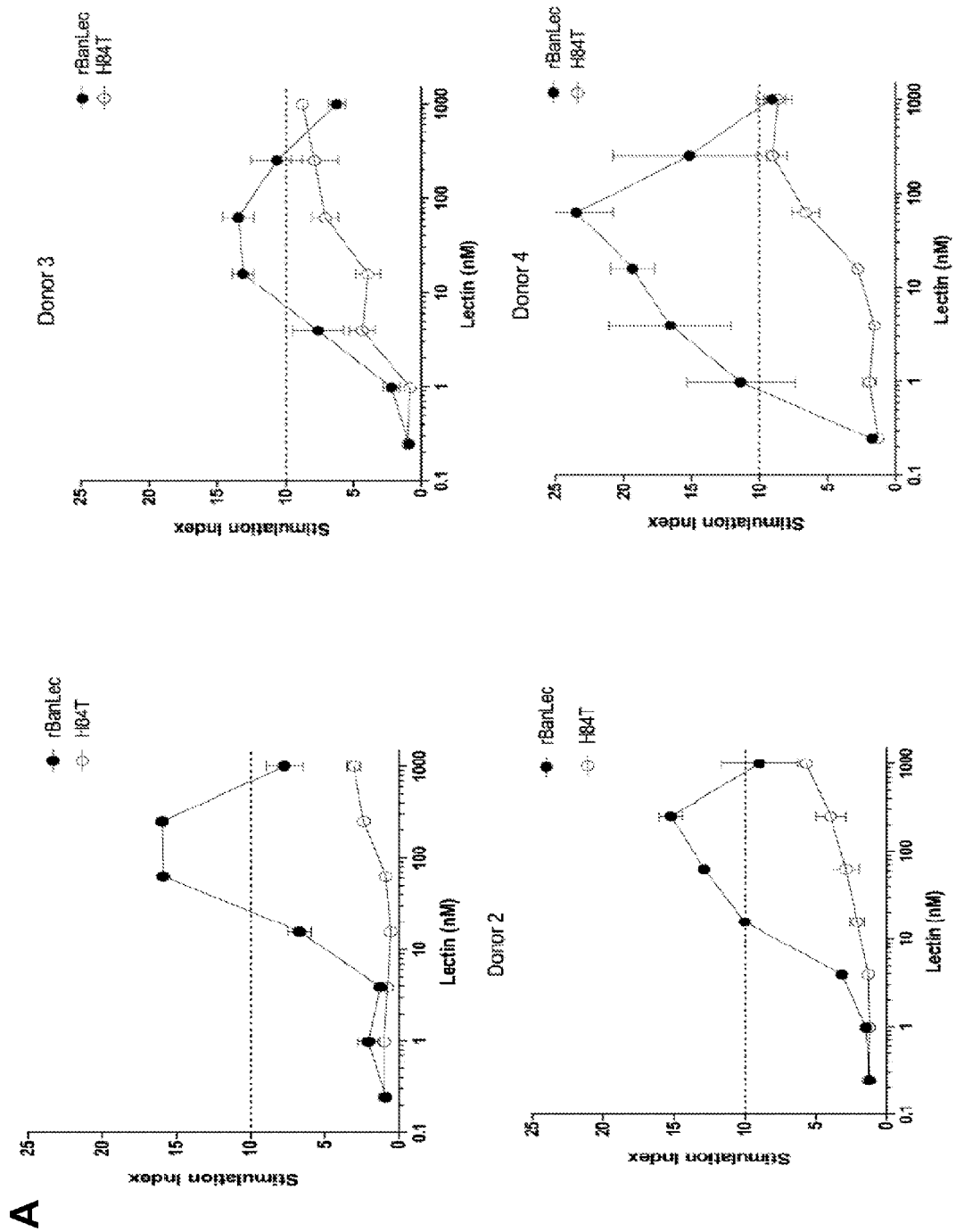
Figure 4:
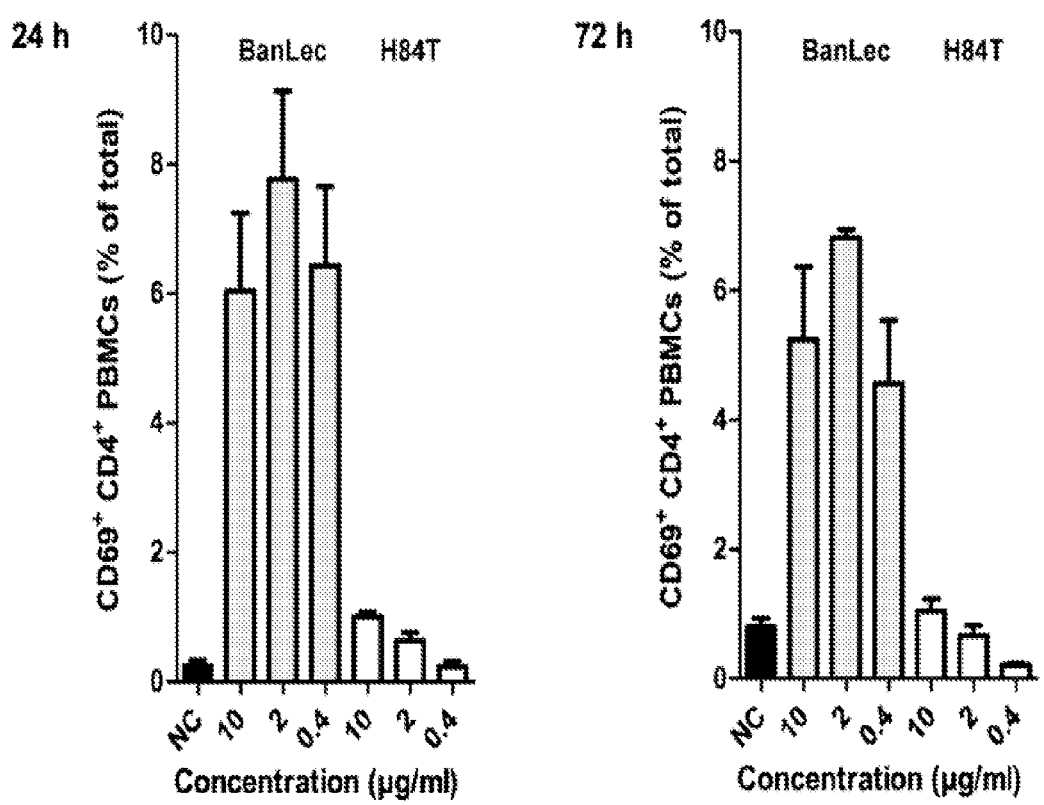
Figure 4:
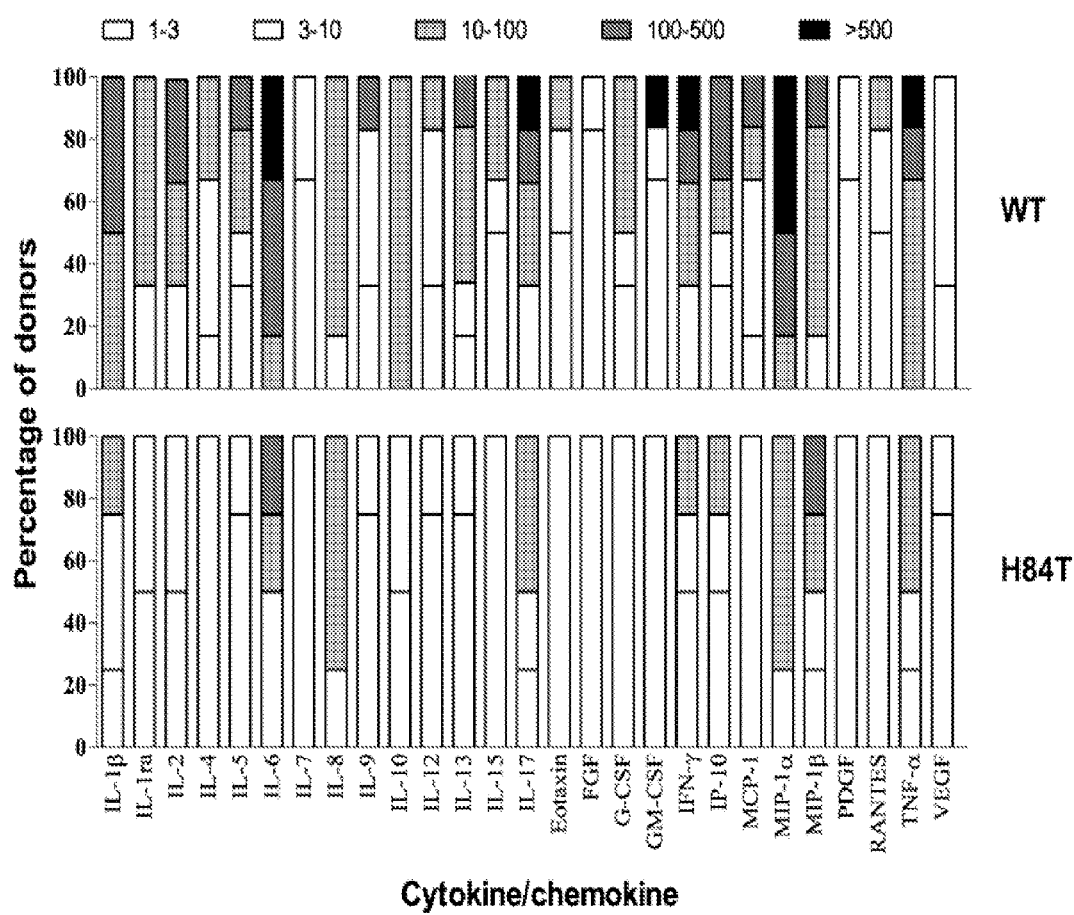
Figure 4:
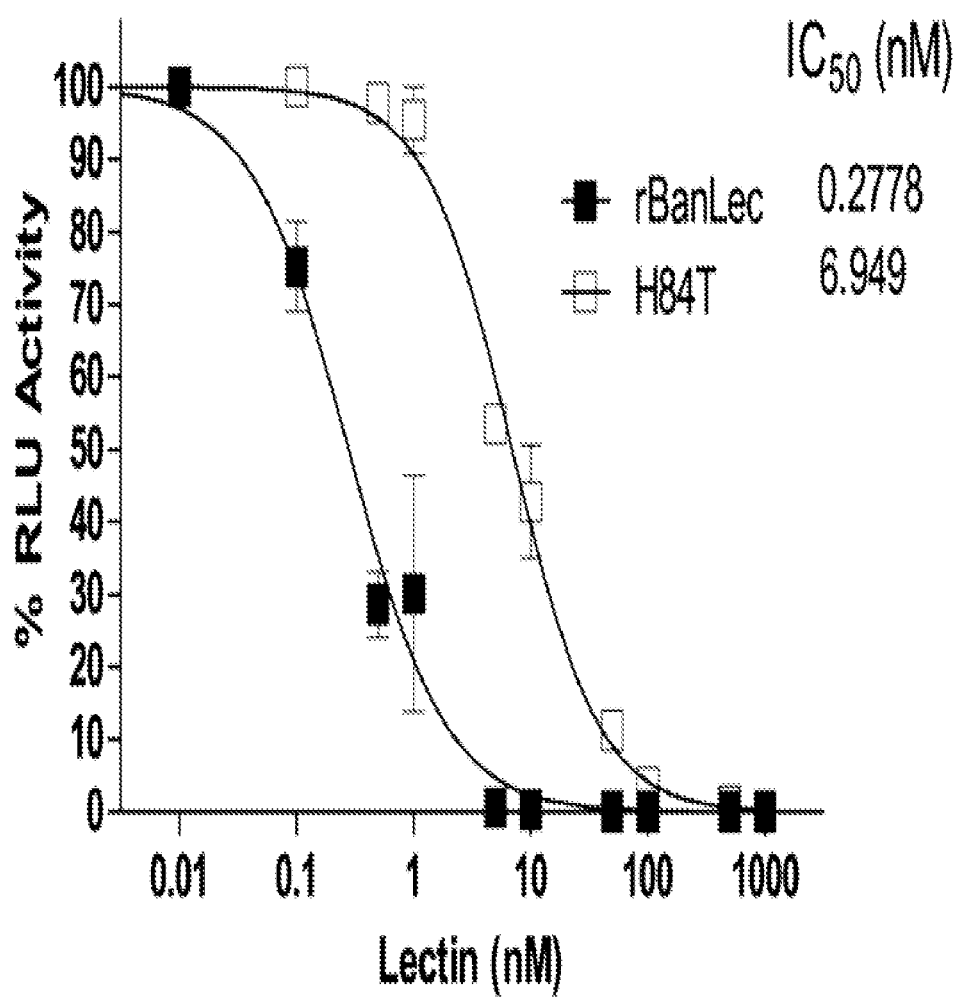
Figure 5:
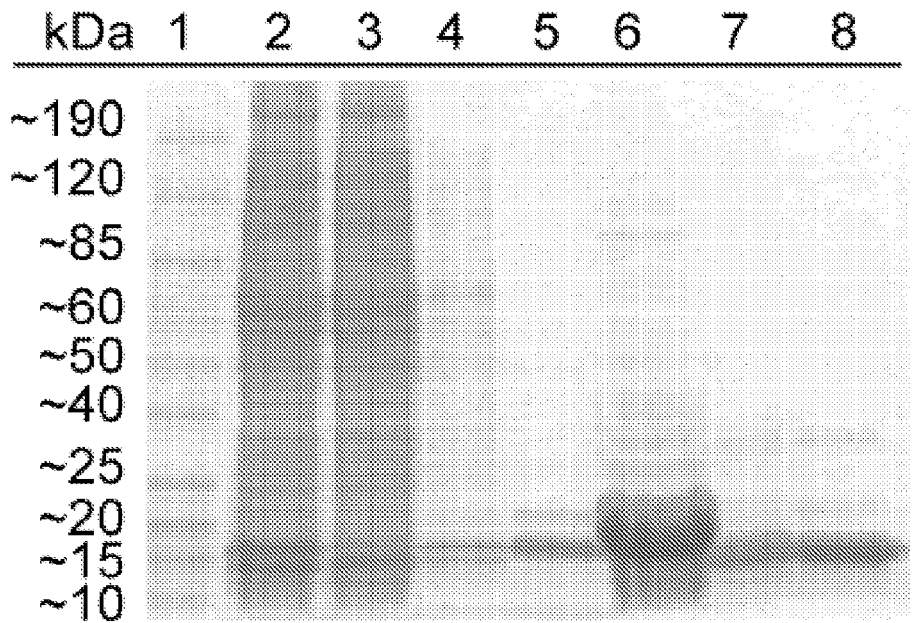

Multiple variants of BanLec containing different substitutions of H84 were constructed, purified, and tested for mitogenic and pro-inflammatory activity. FIG. 3 shows anti-HIV-1 activities of natural and recombinant BanLec. One variant, H84T, did not stimulate the proliferation of lymphocytes at concentrations up to 1 µM (FIG. 4A). Comparison of the pro-inflammatory activity of BanLec and H84T was further determined by measuring upregulation of the activation marker CD69 on CD4+ peripheral blood mononuclear cells (PBMC) and induction of pro-inflammatory cytokines and chemokines. Since upregulation of CD69 on CD4+ T cells is associated with increased susceptibility to HIV-1 infection, expression levels of this marker were measured after 24 and 72 hours of exposure to lectin (Santoni de Sio et al., PLoS One, 2009, 4(8): p. e6571). Increased cell surface expression of CD69 was observed for BanLec-treated CD4+ PBMC. However, the H84T variant induced relatively little upregulation of this activation marker, indicating that this mutation substantially reduces BanLec's potential to stimulate mononuclear cells and cause adverse effects (FIG. 4B).

Figure 6:
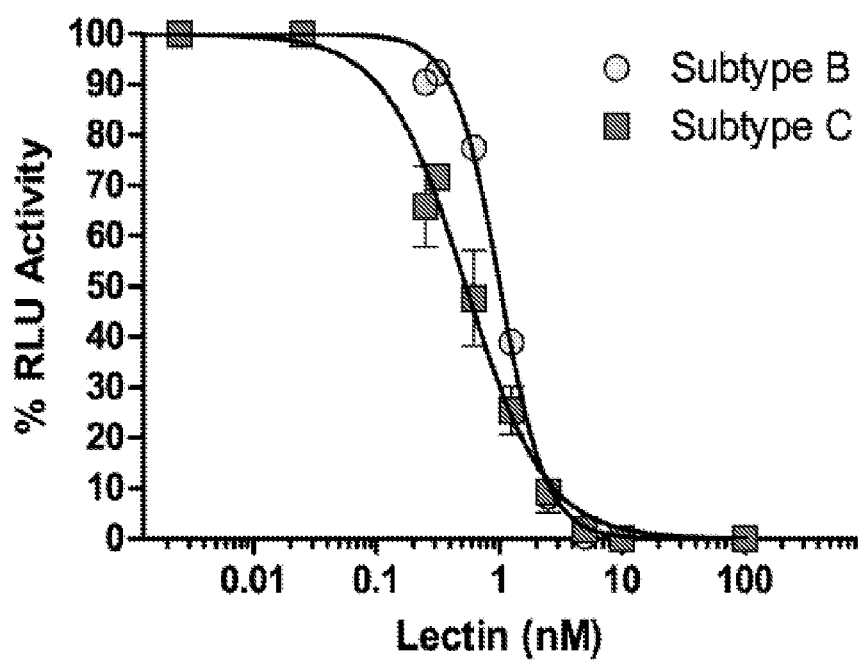

A number of cytokines and chemokines have demonstrated ability to modulate HIV-1 replication. Experiments were conducted to determine whether cellular activation by lectins leads to increased production of pro-HIV replication factors and a non-mitogenic lectin such as H84T does not. This was determined by isolating PBMC from multiple donors and testing whether cytokine/chemokine production was stimulated by BanLec or the H84T variant. Since the relative cytokine production among donors is widely variable, the cytokine responses were grouped over several intervals of production: 1-3, 10-100, 100-500, and 500+ fold over background. Wild-type BanLec caused a large increase in the production of multiple cytokines. The H84T variant induced a markedly reduced production of cytokines and chemokines when compared to the wild-type lectin (FIG. 4C). The anti-HIV activity of the H84T variant was then compared to that of wild-type BanLec and, while there was a very modest loss in anti-HIV activity, the $IC_{50}$ of the H84T was still in the low nanomolar range (FIG. 4D). These results demonstrate that an anti-HIV-1 lectin's mitogenic activity can be separated from its anti-viral activity by targeted engineering. FIG. 6 shows that BanLec inhibits HIV-1 containing consensus subtype B and subtype C envelopes.

To elucidate how the lectin can have markedly decreased mitogenic and pro-inflammatory activity while maintaining anti-HIV-1 activity, the binding properties of the H84T variant and wild-type BanLec were compared. Using isothermal calorimetry, the binding affinities for the monosaccharide ligand methyl-α-D-mannopyranoside were found to be similar: 383 and 358 $mM^{-1}$ for rBanLec and H84T, respectively. The ability to agglutinate rabbit red blood cells is common among mannose-specific lectins and is thought to be dependent on recognition of high-mannose structures found on the cell and the ability to cross-link antigen due to multivalency. When tested for this property, the minimal concentration for agglutination was 3 μg/ml and 437 μg/ml for rBanLec and H84T, respectively. This indicates that H84T is unable to bind and/or cross-link carbohydrate structures found on the rabbit red blood cells. In addition, it was found that the non-mitogenic lectin GRFT required a high concentration for agglutination (600 μg/ml). The present invention is not limited to a particular mechanism. Indeed, an understanding of the mechanism is not necessary to practice the present invention. Nonetheless, one possible explanation for the reduced mitogenic activity observed for the mutant is that the H84T mutation results in a change that hinders the binding of specific high-mannose carbohydrate structures.

Figure 7:
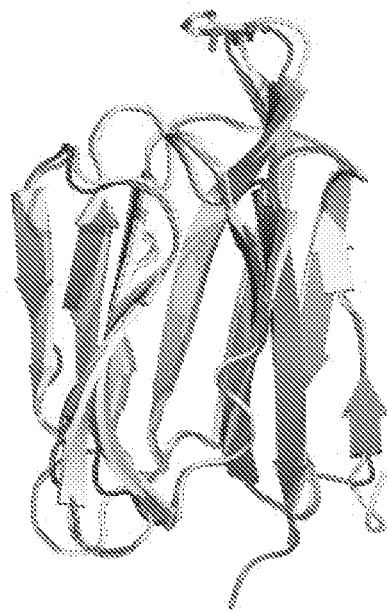
Figure 8:
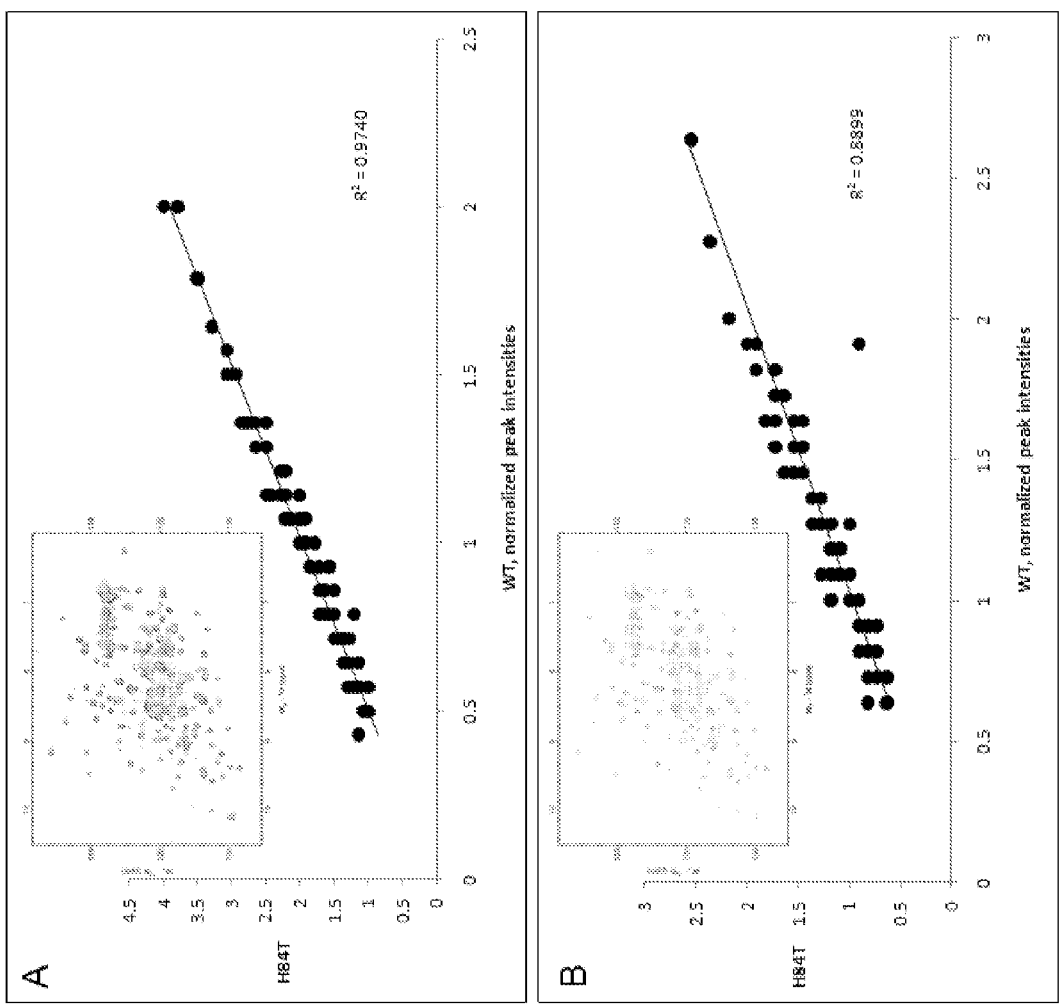

To further explore possible explanations for the reduced mitogenic activity of the H84T variant, protein structure was investigated. Since the mutation is found in an amino acid loop that is thought to play a role in carbohydrate binding, mutations in this region may lead to structural alterations that affect carbohydrate recognition. This alternation in the lectin's configuration then leads to modified carbohydrate specificity and affinity. X-ray crystallography revealed no structural differences when compared to the previously determined structure (FIG. 7A). Because X-ray crystallography is unable to observe changes in dynamic structures, and since this loop is thought to sample multiple conformations, NMR was used to measure structural and dynamic changes in rBanLec and the H84T in the free as well as sugar-bound states. Overlay of $^{1}H$-$^{15}N$ HSQC spectra of the wild-type and mutant in free and sugar bound states shows no change in chemical shifts, indicating similar backbone structure of the two proteins. However, close monitoring of the intensities of the two proteins in free and bound state reveals an interesting drop in intensity for a single residue from rBanLec to the H84T mutant, which occurs only in the sugar-bound state (FIG. 9). This indicates a change in the dynamics of the H84T variant when bound to sugar that alters its binding behavior. Thus, the H84T substitution causes a minor change in the structure of the lectin, altering its carbohydrate binding properties and affecting cellular stimulation but not binding to HIV-1 and inhibiting of viral infection.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

The invention claimed is:

1. A composition comprising a variant BanLec polypeptide, wherein said variant BanLec polypeptide is selected from the group consisting of the amino acid sequence of SEQ ID NOs: 1-3.

2. The composition of claim 1, wherein said variant BanLec polypeptide is encoded by the nucleic acid sequence selected from the group consisting of SEQ ID NOs:4-6.

3. The composition of claim 1, wherein said composition is a pharmaceutical composition comprising a pharmaceutically acceptable carrier.

4. A method of treating HIV or HCV infection in a patient in need thereof comprising administering a composition of claim 1.

5. An expression vector comprising a nucleic acid encoding the amino acid sequence of claim 1.

6. The expression vector of claim 5, wherein said expression vector further comprises a protein purification tag.

7. A non-human host cell comprising the expression vector of claim 6.

* * * * *